US009568437B2

(12) United States Patent
Matsumoto et al.

(10) Patent No.: US 9,568,437 B2
(45) Date of Patent: Feb. 14, 2017

(54) INSPECTION DEVICE

(71) Applicant: Hitachi High-Technologies Corporation, Minato-ku, Tokyo (JP)

(72) Inventors: Shunichi Matsumoto, Tokyo (JP); Akira Hamamatsu, Tokyo (JP); Takahiro Jingu, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 0 days.

(21) Appl. No.: 14/895,618

(22) PCT Filed: May 19, 2014

(86) PCT No.: PCT/JP2014/063146
§ 371 (c)(1),
(2) Date: Dec. 3, 2015

(87) PCT Pub. No.: WO2015/011968
PCT Pub. Date: Jan. 29, 2015

(65) Prior Publication Data
US 2016/0139059 A1    May 19, 2016

(30) Foreign Application Priority Data

Jul. 24, 2013   (JP) .................................. 2013-153172

(51) Int. Cl.
*G01J 3/00*       (2006.01)
*G01N 21/00*    (2006.01)
(Continued)

(52) U.S. Cl.
CPC ...... *G01N 21/8806* (2013.01); *G01N 21/9501* (2013.01); *G01N 21/956* (2013.01);
(Continued)

(58) Field of Classification Search
CPC .................................. G01N 21/00; G01J 3/00
(Continued)

(56) References Cited

U.S. PATENT DOCUMENTS 5,903,342 A    5/1999  Yatsugake et al.
7,436,505 B2 * 10/2008  Belyaev ............. G01N 21/9501
                                                                   356/237.2

(Continued)

FOREIGN PATENT DOCUMENTS

JP          6-349715 A      12/1994
JP       2002-188999 A       7/2002
(Continued)

OTHER PUBLICATIONS

International Search Report (PCT/ISA/210) issued in counterpart International Application No. PCT/JP2014/063146 dated Jul. 22, 2014, with English translation (Four (4) pages).
(Continued)

Primary Examiner — Roy M Punnoose
(74) Attorney, Agent, or Firm — Crowell & Moring LLP

(57) ABSTRACT

An inspection device is required to detect a minute defect, that is, to have high sensitivity as semiconductor devices become finer. There are some approaches for improving the sensitivity. One is to shorten the wavelength of illuminating light radiated onto a sample. This is because, assuming that the wavelength of the illuminating light is $\lambda$, $I \propto \lambda^{-4}$ is established between the magnitude of scattered light is I and $\lambda$. Another approach is to use illuminating light including multiple wavelengths. An approach for taking in more scattered light generated from the sample is also possible. However, an optical system suitable for these approaches has not been sufficiently found in conventional techniques. One feature of the present invention is to detect a defect by using a Wolter optical system including a Wolter mirror.

20 Claims, 12 Drawing Sheets

(51) Int. Cl.
  *G01N 21/88* (2006.01)
  *G01N 21/956* (2006.01)
  *G01N 21/95* (2006.01)
(52) U.S. Cl.
  CPC ............ *G01N 2201/0636* (2013.01); *G01N 2201/06113* (2013.01)
(58) Field of Classification Search
  USPC .......................................................... 356/51
  See application file for complete search history.

(56) References Cited

U.S. PATENT DOCUMENTS

| | | | | |
|---|---|---|---|---|
| 7,952,701 | B2* | 5/2011 | Matsui | ............ G01N 21/9501 356/237.1 |
| 8,160,352 | B2* | 4/2012 | Matsui | ............ G01N 21/8806 382/145 |
| 8,823,935 | B1* | 9/2014 | Meeks | ............ G01N 21/8806 356/237.4 |
| 2002/0041374 | A1 | 4/2002 | Ohshima et al. | |
| 2007/0229809 | A1* | 10/2007 | Belyaev | ............ G01N 21/9501 356/237.2 |
| 2009/0066940 | A1 | 3/2009 | Matsui | |
| 2010/0096557 | A1 | 4/2010 | Zocchi et al. | |
| 2010/0118310 | A1 | 5/2010 | Matsui | |
| 2011/0075135 | A1* | 3/2011 | Matsui | ............ G01N 21/8806 356/237.3 |
| 2012/0176611 | A1 | 7/2012 | Matsui | |
| 2014/0253912 | A1 | 9/2014 | Honda et al. | |

FOREIGN PATENT DOCUMENTS

| | | |
|---|---|---|
| JP | 2007-279040 A | 10/2007 |
| JP | 2009-68903 A | 4/2009 |
| JP | 2010-503882 A | 2/2010 |
| JP | 2011-158356 A | 8/2011 |
| JP | 2013-108950 A | 6/2013 |

OTHER PUBLICATIONS

Japanese language Written Opinion (PCT/ISA/237) issued in counterpart International Application No. PCT/JP2014/063146 dated Jul. 22, 2014 (Six (6) pages).

* cited by examiner

INSPECTION DEVICE

TECHNICAL FIELD

The present invention relates to a device and a method for detecting an abnormality on a sample. For example, the present invention relates to an inspection device that inspects a minute defect on a surface of a sample, determines at least one of the position, the type, and the dimension of the defect, and outputs the determination result, and also relates to a faint light detection method and a faint light detection detector.

In a manufacturing line of a semiconductor substrate, a thin film substrate, or the like, inspection is performed to detect a defect on a surface of the semiconductor substrate, the thin film substrate, or the like in order to retain or improve a yield of products. A so-called inspection device is used in the defect inspection. Patent Literature 1 describes a conventional technique, for example.

CITATION LIST

Patent Literature

Patent Literature 1: U.S. Pat. No. 5,903,342

SUMMARY OF INVENTION

Technical Problem

The inspection device is required to detect a minute defect, that is, to have high sensitivity, as semiconductor devices become finer. There are some approaches for improving the sensitivity. One is to shorten the wavelength of illuminating light that is radiated onto a sample. This is because, assuming that the wavelength of the illuminating light is $\lambda$, $I \propto \lambda^{-4}$ is established between the magnitude of scattered light is I and $\lambda$. Another approach is to use illuminating light including multiple wavelengths. Further, an approach is possible that takes in more scattered light generated from the sample. However, an optical system suitable for these approaches has not been sufficiently found in conventional techniques.

Solution to Problem

One feature of the present invention is to detect a defect by using a Wolter optical system including a Wolter mirror.

Advantageous Effects of Invention

According to the present invention, inspection with high sensitivity can be performed.

DESCRIPTION OF EMBODIMENTS

Figure 1:
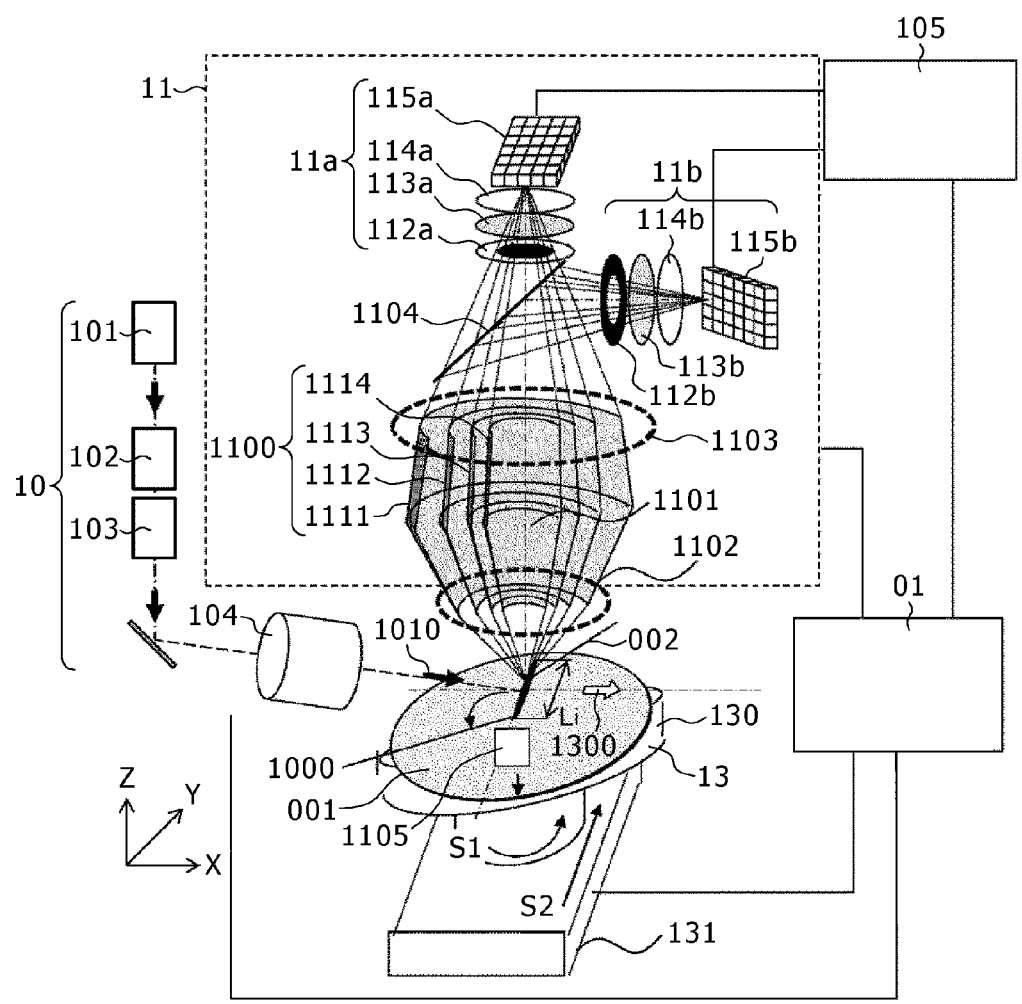
FIG. 1 is an explanatory diagram of a device configuration in a first embodiment.

Embodiments of the present invention are described below, referring to the drawings. It is noted that the present invention is not limited to the embodiments described below, and may include various modifications. The following embodiments are described in detail for the purpose of easy understanding of the present invention. The present invention is not intended to be limited to the one provided with all the structures of the description. The structure of any one of the embodiments may be partially replaced with that of the other embodiment. It is also possible to add the structure of any one of the embodiments to that of the other embodiment. It is also possible to have the part of the structure of the respective embodiments added to, removed from, and replaced with the other structure. The term "wafer" is a term having a broad meaning including not only a silicon wafer in a strict meaning but also a substrate with a film formed thereon and another sample.

First Embodiment

FIG. 1 illustrates a configuration example of a defect inspection device according to this embodiment. The defect inspection device 1 of this embodiment is configured to include an illumination optical system unit 10, a detection optical system unit 11, a data processing unit 12, a stage unit 13, and an overall control unit 01.

Figure 2:
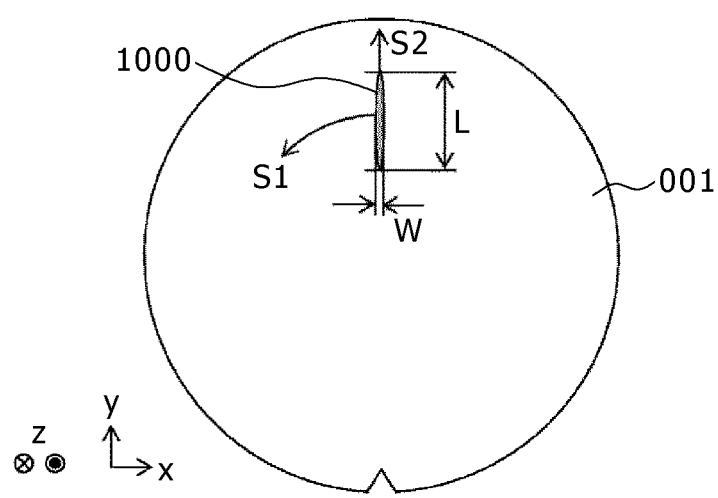
FIG. 2 is an explanatory diagram of a shape of an illuminated region on a sample surface and a scanning direction.
Figure 3:
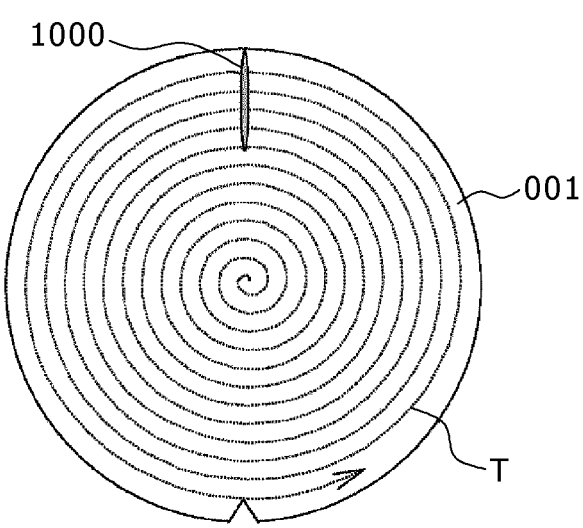
FIG. 3 is an explanatory diagram of a track of an illuminating spot formed by scanning.

The stage unit 13 includes a translation stage 130, a rotary stage 131, and a Z-stage for adjusting the height of a wafer surface. As shown in FIGS. 2 and 3, a longitudinal direction of a thin linear illuminated region 1000 formed on a surface of a wafer 001 by the wafer illumination optical system unit 10 is defined as S2, and a direction substantially perpendicular to the direction S2 is defined as S1. Scanning in a circumferential direction S1 of a circle centered on a rotation axis of the rotary stage is achieved by rotational motion of the rotary stage, while scanning in a translation direction S2 of the translation stage is achieved by translational motion of the translation stage. During scanning along the entire circumference of the sample in the scanning direction S1, scanning in the scanning direction S2 is performed over a distance equal to or shorter than a longitudinal length of the thin linear illuminated region 1000. By such scanning, an illuminating spot travels along a spiral track T on the wafer 001, so that the surface of the wafer 001 is entirely scanned. In this manner, inspection of the entire surface of the wafer can be performed.

When the wafer 001 deviates from a focusing range of a Wolter optical system 1100, a first detection unit 11a, and a second detection unit 11b during scanning, a state of faint scattered light detected by parallel photon counting sensors 115a and 115b changes to deteriorate defect detection sensitivity. Therefore, it is desirable that the z-position of the wafer surface is controlled by the Z stage to always be in the focusing range of the Wolter optical system 1100, the first detection unit 11a, and the second detection unit 11b during scanning. Detection of the z-position of the wafer surface is performed by a wafer-surface z-position detection unit 1105.

Returning of FIG. 1, the illumination optical system unit 10 includes a light source 101, polarized state control means 102, a beam shaping unit 103, and a thin linear converging optical system 104. In this configuration, illuminating light emitted from the light source 101 is transmitted through the polarized state control means 102 and the beam shaping unit 103, and is introduced into the thin linear converging optical system 104. The polarized state control means 102 is formed by a polarizer such as a half-wave plate or a quarter-wave plate, is provided with drive means (not shown) that allows to be rotated around the optical axis of the illumination optical system, and adjusts a polarized state of the illuminating light for illuminating the wafer 001 placed on the stage unit 13. The beam shaping unit 103 is an optical unit forming thin linear illumination that will be described later, and is formed by a beam expander, anamorphic prism, or the like. The thin linear converging optical system 104 is formed by a cylindrical lens and the like, and radiates a thin linear illuminated region 1000 of the wafer (substrate) 001 with the illuminating light shaped into a thin line. This embodiment is described on the assumption that a width direction of the thin linear illumination (i.e., a direction perpendicular to the longitudinal direction of the thin linear illuminated region) is defined as a stage scanning direction (x-direction), and a longitudinal direction of the thin linear illuminated region is defined as y-direction, as shown in FIG. 1.

In this embodiment, thin linear illumination that illuminates a narrow illuminated region is provided, as described above. One of the objects of this illumination is to improve an inspection throughput by increasing illuminance of the illumination (an energy density of the illumination) to an inspection object. Therefore, it is desirable to use a laser light source radiating linearly polarized light that can be well converged and is highly coherent, as the light source 101. Further, it is effective to shorten the wavelength of the light source in order to increase scattered light from the defect. The light source 101 of this embodiment includes a UV (Ultra Violet) laser. Furthermore, the light source 101 of this embodiment can use at least one of a 355-nm solid-state laser of YAG (Yttrium Aluminum Garnet)-THG (Third Harmonic Generation), a 266-nm solid-state laser of YAG-FHG (Fourth Harmonic Generation), and a solid-state laser having a wavelength of 213 nm, 199 nm, and 193 nm generated as sum frequencies of fundamental waves of the YAG-FHG laser and a YAG laser. In other words, the illumination optical unit 10 of this embodiment supplies substantially single-wavelength light to the wafer 001 in some cases, and the light source 101 includes a so-called broad-band light source and supplies light containing a plurality of wavelengths in other cases.

Scattered light from the illuminated region 1000 is converged by the Wolter optical system 1100 to form an image. The Wolter optical system 1110 includes a plurality of Wolter mirror 1111 to 1114. The Wolter mirrors 1111 to 1114 are stacked to surround a normal 1101 of a surface on which the wafer 001 is to be placed. The normal 1101 passes through a light-converging end 1102 and a light-exiting end 1103 of the Wolter optical system 1100. More specifically, the normal 1101 passes through a light-converging end and a light-exiting end of the Wolter mirror 1111 that is the innermost one of the Wolter mirrors. In this embodiment, an optical axis 1101 of the Wolter optical system 1100 is substantially coincident with the normal of the surface on which the wafer 001 is to be placed and is substantially parallel thereto. For example, the Wolter optical system 1100 can be described as an optical system converging light generated from any sample because of formation of the illuminated region 1000 (that is, light in a broad sense including regularly reflected light and scattered light).

In this embodiment, the illuminating light 1010 is incident on the wafer 001 obliquely at a predetermined angle of incidence with respect to the wafer 001 from the outside of the Wolter optical system 1100, and the Wolter optical system 1100 detects the scattered light. Therefore, the inspection apparatus of this embodiment can be said as a dark field type.

The light converged by the Wolter optical system 1100 is split by a splitting optical element 1104 (for example, a half-mirror or a polarized beam splitter) and is incident on the first detection unit 11a and the second detection unit 11b.

The first detection unit 11a includes a spatial filter 112a, a polarizing filter 113a, an image forming lens 114a, and a parallel photon counting sensor 115a. The second detection unit 11b includes a spatial filter 112b, a polarizing filter 113b, an image forming lens 114b, and a parallel photon counting sensor 115b.

The light transmitted through the splitting optical element 1104 forms on an image on the parallel photon counting sensor 115a, while the light reflected by the splitting optical element 1104 forms an image on the parallel photon counting sensor 115b. More specifically, a scattered light image (a point image) of the defect on the wafer 001 is formed over a plurality of elements of the parallel photon counting sensor 115a. Also in the second detection unit 11b, a scattered light image (a point image) of the defect on the wafer is formed over a plurality of elements of the parallel photon counting sensor 115b. Because the Wolter optical system 100 has an image forming function, the image forming lenses 114a and 114b are not necessarily provided.

The spatial filter 112a, 112b blocks background scattered light generated by roughness of the wafer 001 and the like to reduce background light noises in detection and improve defect detection sensitivity. The polarizing filter (e.g., a polarizer) 113a, 113b is used for filtering a specific polarized component from the detected scattered light to reduce the background light noises and improve the defect detection sensitivity.

The parallel photon counting sensor 115a, 115b converts the detected scattered light into an electric signal by photoelectric conversion. For this sensor, a method is known that measures a total of pulse currents generated by incidence of photons on respective APD elements of a detector in which the APD elements are two-dimensionally arranged. This detector is an element called as Silicon Photomultiplier, Pixelated Photon Detector, or Avalanche Photodiode Array, for example.

The signals from the parallel photon counting sensors 115a and 115b are transmitted to the signal processing unit 105 where defect detection is performed.

Figure 4:
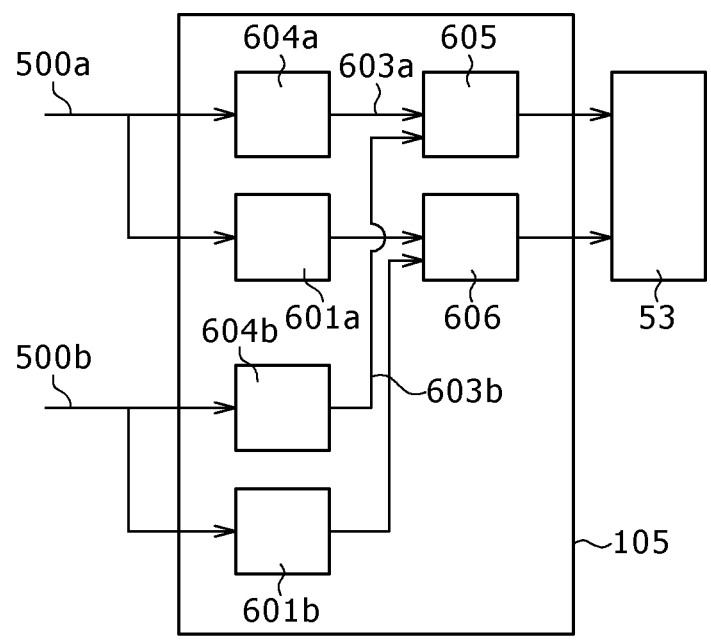
FIG. 4 is an explanatory diagram of a signal processing unit.

The signal processing unit 105 performs classification of various defect types and estimation of a defect dimension with high accuracy based on the scattered light signals obtained by photoelectric conversion by the first and second parallel photon counting sensors 115a and 115b. A specific configuration of the signal processing unit 105 is described referring to FIG. 4. Actually, each of the first detection unit 11a and the second detection unit 11b outputs a plurality of signals for respective channels of the parallel photon detection sensors 115a and 115b. Although the description is made with respect to a signal of one of those channels, the same process is performed for other channels in parallel.

Output signals 500a and 500b corresponding to the amounts of detected scattered light output from the parallel photon detection sensors 115a and 115b are input to high-pass filters 604a and 604b, respectively. Defect signals 603a and 603b are extracted by the high-pass filters 604a and 604b from the corresponding output signals 500a and 500b, and are input to a defect determining unit 605.

Because scanning in the aforementioned stage scanning is performed in the width direction S1 of the illuminated region 1000 (that is, the circumferential direction of the wafer), a waveform obtained by enlarging or reducing a illuminance distribution profile of the illuminated region 1000 in the direction S1 is obtained as a waveform of the defect signal. Therefore, a frequency band including the waveform of the defect signal is allowed to pass through the high-pass filter 604a, 604b, and cut a frequency band and a direct current component that include relatively much noises are cut by the high-pass filter 604a, 604b. Thus, an S/N ratio of the defect signal 603a, 603b is improved.

Each of the high-pass filters 604a and 604b is formed by a high-pass filter designed to have a specific cut-off frequency and block components having frequencies equal to or higher than the cut-off frequency, or a band-pass filter, or a FIR (Finite Impulse Response) filter having a similar waveform to the waveform of the defect signal on which the shape of the illuminance distribution of the illuminated region 1000 is reflected.

The defect determining unit 605 performs threshold processing for an input of the signal including the defect waveform output from each of the high-pass filters 604a and 604b to determine the presence or absence of the defect. In other words, because the defect signals based on the detection signals from the plural of detection optical systems are input to the defect determining unit 605, the defect determining unit 605 can perform defect inspection with higher sensitivity as compared with defect detection based on a single defect signal, by performing the threshold processing for a sum or a weighted average of the defect signals or obtaining OR or AND for a group of defects extracted by the threshold processing for the defect signals in the same coordinate system set on the surface of the wafer.

Further, for a portion determined to be include a defect, the defect determining unit 605 provides a defect coordinate indicating the position of the defect in the wafer and an estimation value of the dimension of the defect, which are calculated based on the defect waveform and a sensitivity information signal, to the display unit 53 as defect information, thereby outputting the defect information to the display unit or the like. The defect coordinate is calculated by using a center of gravity of the defect waveform as a reference. The dimension of the defect is calculated based on an integral value or the maximum value of the defect waveform.

In addition, the output signals 500a and 500b are input to low-pass filters 601a and 601b, respectively. Each of the low-pass filters 601a and 601b outputs a low frequency component and a direct current component corresponding to the amount of scattered light (haze) from minute roughness in the illuminated region 1000 on the wafer. The outputs of the low-pass filters 601a and 601b are input to a haze processing unit 606 and are subjected to processing of haze information therein. That is, the haze processing unit 606 outputs a signal corresponding to the magnitude of the haze for every position on the wafer as a haze signal, from the magnitude of the input signal from each of the low-pass filters 601a and 601b. It is possible to derive a state of the surface of the wafer 001 together from the haze information.

Figure 5:
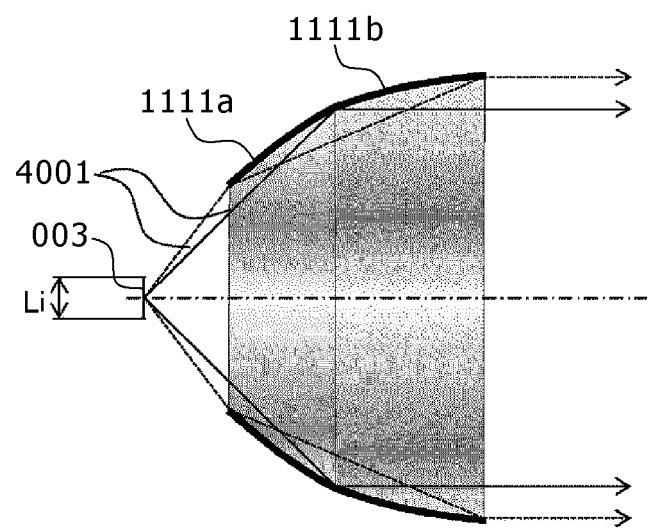
FIG. 5 is an explanatory diagram of a Wolter mirror 1111.
Figure 6:
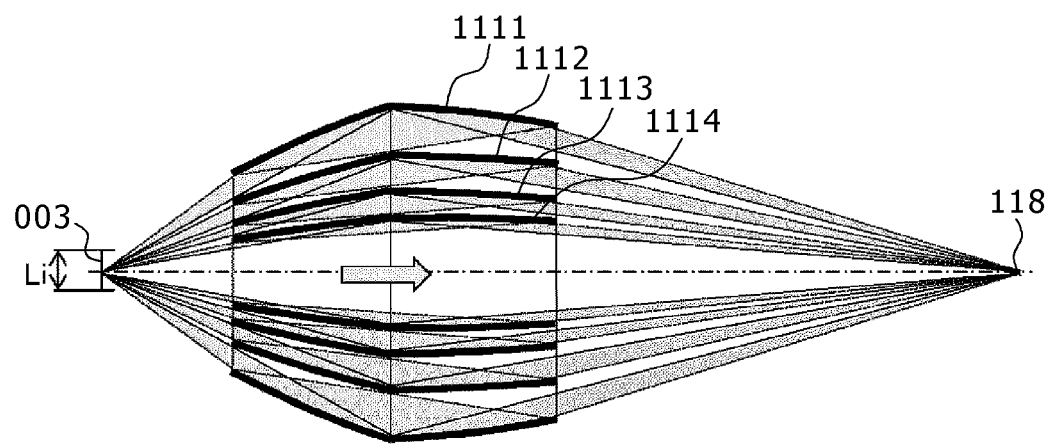
FIG. 6 is an explanatory diagram of a Wolter optical system 1100.

Next, the Wolter optical system 1100 is described in detail, with reference to FIG. 5. FIG. 5 is a cross-sectional view of the Wolter mirror 1111. A first reflecting surface 1111a of the Wolter mirror 1111 reflects scattered light 4001 from a cross section 003 of the illuminated region 1000 towards a second reflecting surface 1111b. The light reflected by the second reflecting surface 1111b travels towards a point 118 in FIG. 6. The same can be applied to the Wolter mirrors 1112 to 1114, as shown in FIG. 6. The point 118 is optically substantially coincident with at least one light-receiving surface of the parallel photon counting sensor 115a, 115b. Therefore, the scattered light from the wafer 001 is converged to form a point image on at least one light-receiving surface of the parallel photon counting sensor 115a, 115b.

The Wolter mirrors 1111 to 114 can be described in various ways. For example, they can be described as optical elements each having two reflecting surfaces (more specifically, two hyperboloids) formed at different positions in a hollow case and can also be described as optical elements each formed by a combination of a paraboloid and a hyperboloid.

One feature of the Wolter optical system 1100 is in that it constitutes a substantially totally reflecting optical system. Therefore, the Wolter optical system 1100 is substantially free from light absorption by a lens occurring in a case where x-rays or vacuum ultraviolet rays are used as the illuminating light and the lens is used for converging those rays. Further, the Wolter optical system 1100 is substantially free from color aberration occurring in a case of using a refracting optical system such as a lens. Therefore, the Wolter optical system 1100 is also suitable when broad-band illumination is supplied to the wafer 001. Furthermore, a large objective lens or an optical element that is for taking more scattered light in is also substantially unnecessary. Therefore, the scattered light can be easily taken in. Consequently, a detection optical system can be provided which is suitable for increasing the sensitivity, particularly, reduction in the wavelength of the illuminating light or increasing the number of wavelengths of the illuminating light.

Aluminum is used for the first and second reflecting surfaces 1111a and 1111b in some cases. In a case of using x-rays as the illuminating light, gold, platinum, or a multi-layer film may be used so that the x-rays are totally reflected by the first and second reflecting surfaces 1111a and 1111b. Particularly, in a case of using the x-rays as the illuminating light, it is desirable to evacuate an optical path of the illuminating light, an area on the wafer 001, the inside of the Wolter optical system 1100, a path connecting to at least one of the parallel photon counting sensors 115a and 115b to vacuum by an air discharge system, for example, formed by a pump.

Figure 7:
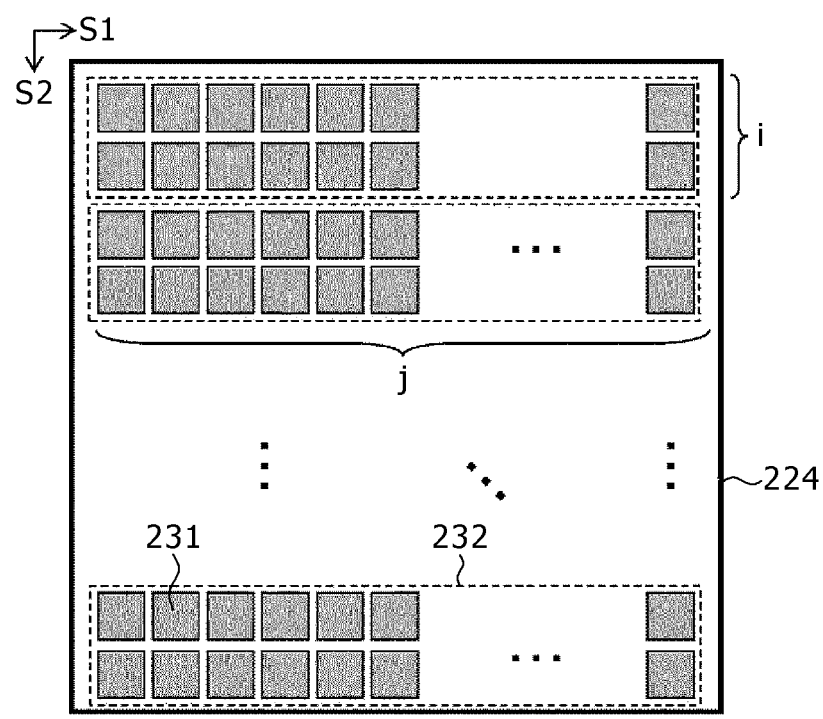
FIG. 7 is an explanatory diagram of a parallel photon counting sensor 115*a*.

Next, the parallel photon counting sensor 115a is described in detail. The following description can be applied to the parallel photon counting sensor 115b. FIG. 7 is an example of the structure of the light receiving surface of the parallel photon counting sensor 115a. The parallel photon counting sensor 115a has the structure in which a plurality of APD elements 231 are two-dimensionally arranged. A voltage is applied to the APD elements 231 so that each of them operates in Geiger mode (having a photo-multiplication factor equal to or larger than $10^5$). When one photon is incident on the APD element 231, a photoelectron is generated in the APD element 231 with a probability in accordance with quantum efficiency of the APD element and is multiplied by the effect of the APD element operating in Geiger mode, so that a pulse-like electric signal is output. Regarding a group of APD elements enclosed by dotted line 232 in FIG. 6 as one unit (ch), pulse-like electric signals respectively generated in i APD elements in the direction S1 and j APD elements in the direction S2 are summed and output. The resultant total signal corresponds to the amount of light detected through photon counting. A plurality of such channels are arranged in the direction S2. This arrangement makes it possible to detect the amount of the scattered light by simultaneous parallel photon counting for each of a plurality of regions in a field of view of the detection system. Because the scattered light detection is performed by counting photons, it is possible to detect faint light and is therefore possible to detect a minute defect, that is, to improve the defect detection sensitivity.

Figure 8:
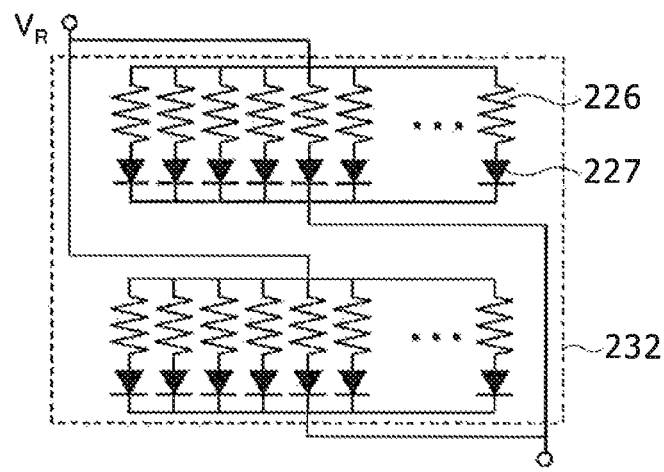
FIG. 8 is a continuing explanatory diagram of the parallel photon counting sensor 115*a*.

FIG. 8 shows an example of a circuit diagram of a circuit equivalent to the group of i×j APD elements forming one channel. A pair of a quenching resistance 226 and an APD 227 in FIG. 8 corresponds to one APD element 231 described referring to FIG. 7. A reverse voltage $V_R$ is applied to each of the APDs 227. Setting of the reverse voltage $V_R$ to be equal to or higher than a breakdown voltage of the APD 227 allows the APD 227 to operate in Geiger mode. With the circuit configuration shown in FIG. 7, an output electric signal (a peak value of a voltage, a current, or the amount of electric charges) is obtained which is in proportion to the total number of photons incident on a region of one channel of the parallel photon counting sensor including the group of i×j APD elements. The output electric signals corresponding to the respective channels are subjected to analog-digital conversion and are output as time series digital signals in parallel.

Even if a plurality of photons are incident within a short period of time, each APD element outputs a pulse signal at substantially the same level as a pulse signal output in a case where only one photon is incident. Therefore, when the number of the incident photons per unit time onto each APD element increases, the total output signal of the single channel is no longer proportional to the number of incident photons, thus deteriorating the linearity of the signal. Further, when the amount of incident light on all the APD elements of the single channel is equal to or larger than a certain amount (approximately one photon per one element on an average), the output signal is saturated. With the configuration in which a number of APD elements are arranged in the directions S1 and S2, it is possible to reduce the amount of the incident light for each pixel, thus ensuring more accurate photon counting. For example, when the number of pixels of one channel having i×j elements arranged in the directions S1 and S2 is set to 1000 pixels, in a case where the quantum efficiency of the APD element is 30%, the light intensity equal to or less than 1000 photons per unit time of detection ensures sufficient linearity. Therefore, the light intensity equal to or less than about 3300 photons can be detected without saturation.

According to this embodiment, defect detection with high sensitivity can be performed. Especially, in a case of using x-rays, vacuum ultraviolet rays, or light including a plurality of wavelengths for illumination, it is possible to perform defect detection with high sensitivity.

In the structure of the parallel photon counting sensor shown in FIG. 7, the light intensity in the direction S1 is not uniform, that is, the light intensity at an end portion of the sensor is weaker than that at the center portion in some cases. When a lenticular lens having a large number of minute cylindrical lenses each with a curvature arranged in the direction S1, a diffracting optical element, or an aspherical lens is used instead of the cylindrical lens as the image forming optical element, the distribution of a single-axis enlarged image of the defect image in the direction S1 can be uniform in intensity. This makes it possible to further enlarge the range of the light intensity in which linearity is ensured or no saturation occurs, while the number of APD elements in the direction S1 is retained.

The thin linear illuminated region 1000 as described above serves to illuminate the substrate so as to be narrowed to the detection range of the parallel photon counting sensors 115a and 115b for improving the efficiency of the illuminating light (because illuminating a region outside the detection range of the sensor is ineffective).

The description is made to the relation among the length of the illuminated region 1000, the optical magnifications of the Wolter optical system 1100 and the detection optical systems 11a and 11b, and the dimensions of the parallel photon counting sensors 115a and 115b. In a case of performing high-speed inspection with high sensitivity, the length L of the illuminated region 1000 is set to approximately 200 μm. It is assumed that a unit including 20 APD elements (25 μm×25 μm) operating in Geiger mode arranged in the direction S2 and 160 APD elements arranged in the direction S1 constitutes one channel, and 8 channels are arranged in the direction S1 to configure each parallel photon counting sensor 105. In this case, the entire length of the parallel photon counting sensor in the direction S1 is 4 mm. When this entire length is compared with the length L of the illuminated region of 200 μm, the optical magnification of the detection unit is 20 times and a pitch of the detection channels projected on the wafer surface is 25 μm.

Under this condition, when a sample is rotated at a rotating speed of 2000 rpm and a feed pitch of the translation stage for each revolution is set to 12.5 μm, a wafer with a diameter of 300 mm has its entire surface scanned in 6 seconds, and a wafer with a diameter of 450 mm has its entire surface scanned in 9 seconds. In this case, the feed pitch of the translation stage for each revolution when rotary scanning of the wafer is performed is set to a half of the pitch of 25 μm of the detection channels projected on the wafer surface. However, the feed pitch is not limited to this value, but may be set to an arbitrary one of 1/(even number) or 1/(odd number) of the detection channels projected onto the wafer surface, or may be set to an arbitrary value without being limited to 1/integer.

Figure 9A:
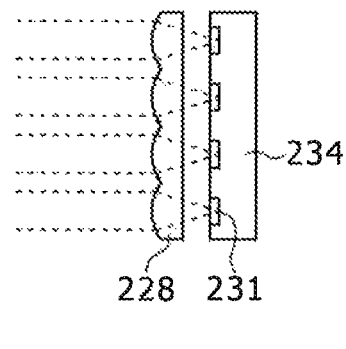
FIGS. 9A, and 9B are explanatory diagrams of a modification of the parallel photon counting sensor 115*a*.

FIG. 9 (a) is a configuration diagram of a first modification of the parallel photon counting sensor 115a, 115b. In a parallel photon counting sensor 224 having arranged APD elements, when each APD element is made small, an area of a dead zone formed by a wiring arranged between the APD elements and a quenching resistance becomes large relative to an effective area of a light receiving portion. This may reduce an aperture ratio of the parallel photon counting sensor and reduce optical detection efficiency. Therefore, a micro-lens array 228 is disposed in front of a light receiving surface 231 of the parallel photon counting sensor 234 as shown in FIG. 9 (a). This arrangement can reduce a ratio of light incident on the dead zone between the elements and improve effective efficiency. The micro-lens array 228 is configured by minute convex lenses arranged at the same pitch as that of the arranged APD elements, and is disposed so that light rays (shown with dotted line in FIG. 9(a)) parallel to a main optical axis of light incident on the parallel photon counting sensor 234 are incident on an area around center of the corresponding light receiving surface 231.

Figure 9B:
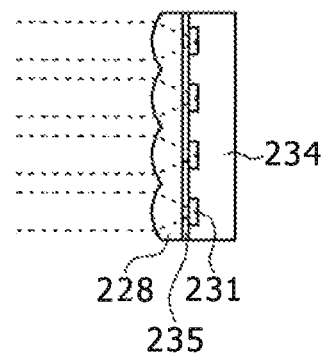

FIG. 9(b) is a configuration diagram of a second modification of the parallel photon counting sensor 115a, 115b. Generally, the APD element is a device using silicon-based material. In a general silicon device, the quantum efficiency is reduced in an ultraviolet region. In order to overcome this problem, silicon nitride based material or gallium nitride based material is used for forming the APD element. Alternatively, it is possible to employ a method for sufficiently increasing conversion efficiency by disposing a wavelength conversion member (scintillator) 235 between the micro-lens array 228 and the parallel photon counting sensor 234 manufactured through a silicon process so that ultraviolet light is converted into long-wavelength light (for example, visible light) to allow incidence of light having a longer wavelength onto the light receiving surface 231 than the wavelength of the light incident on the wavelength conversion material 235, as shown in FIG. 9(b).

Second Embodiment

Next, a second embodiment is described. In the following, a difference between the second embodiment and other embodiments are described.

Scattered light from a defect changes in accordance with at least one of the size of the defect and the type of the defect (a projection defect such as foreign substance or a concave defect such as a damage). This embodiment considers this point.

Figure 10A:
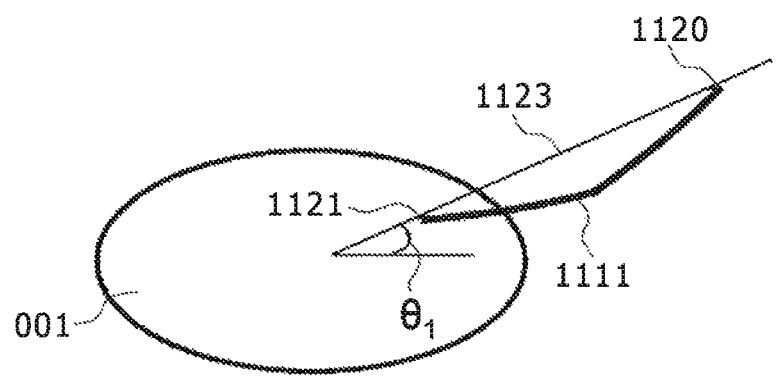
FIGS. 10A and 10B are explanatory diagrams of a second embodiment.

FIG. 10 are diagrams explaining this embodiment. An elevation angle described later can be described in various ways. Here, the elevation angle is described as an angle between a line connecting a light-converging end 1121 with a light-exiting end 1120 and the wafer 001, as shown in FIG. 10(a). In FIG. 10(a), the elevation angle $\theta_1$ is formed to be larger than 0° and equal to or smaller than 45°, for example. The scattered light from minute foreign substance may be scattered at a relatively small elevation angle. Therefore, the arrangement shown in FIG. 10(a) may be suitable for efficiently detecting the scattered light from the minute foreign substance.

Figure 10B:
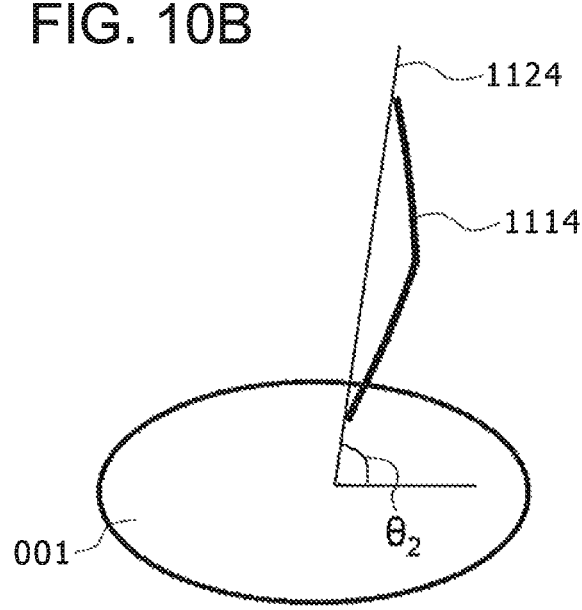

In FIG. 10(b), the elevation angle θ2 is formed to be larger than 45°, for example. The scattered light from the concave defect may be detected at a relatively large elevation angle, although it depends on the angle of incidence of the illuminating light. Therefore, the arrangement shown in FIG. 10(b) may be suitable for efficiently detecting the scattered light from the concave defect. With the aforementioned configurations and arrangements of the Wolter mirrors 1111 and 1114, it is possible to efficiently converge the scattered light from a specific defect to form an image.

Figure 11:
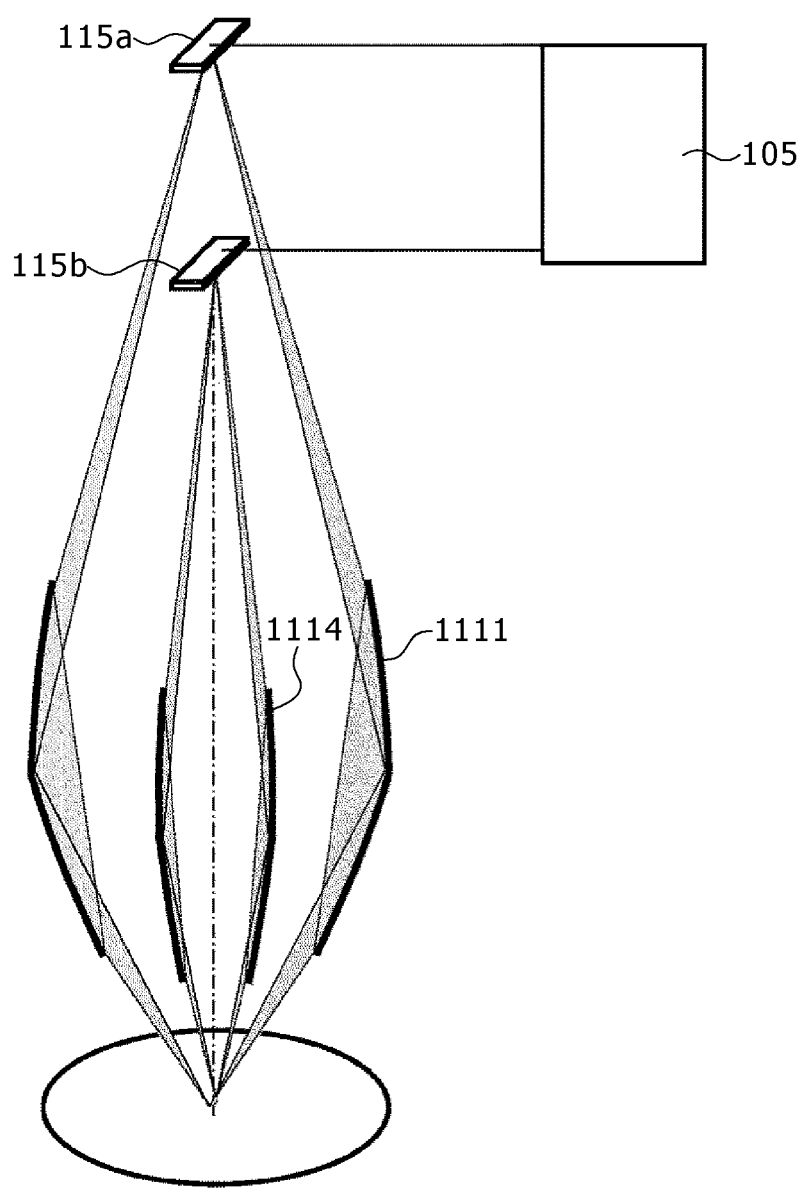
FIG. 11 is continuing explanatory diagram of the second embodiment.

Further, the Wolter mirrors 1111 and 1114 described in FIGS. 10(a) and 10(b) may be configured and arranged to form images at different positions from each other, as shown in FIG. 11, so that the parallel photon counting sensor 115a detects the image of the scattered light from the Wolter mirror 1111, the parallel photon counting sensor 115b detects the image of the scattered light from the Wolter mirror 1114, and signals from the parallel photon counting sensors 115a and 115b are compared in the signal processing unit. This allows classification of the type of the defect.

Third Embodiment

Next, a third embodiment is described. Another modification can be considered for the arrangement of the Wolter optical system 1100. In the following, a difference between the third embodiment and other embodiments is mainly described.

Figure 12:
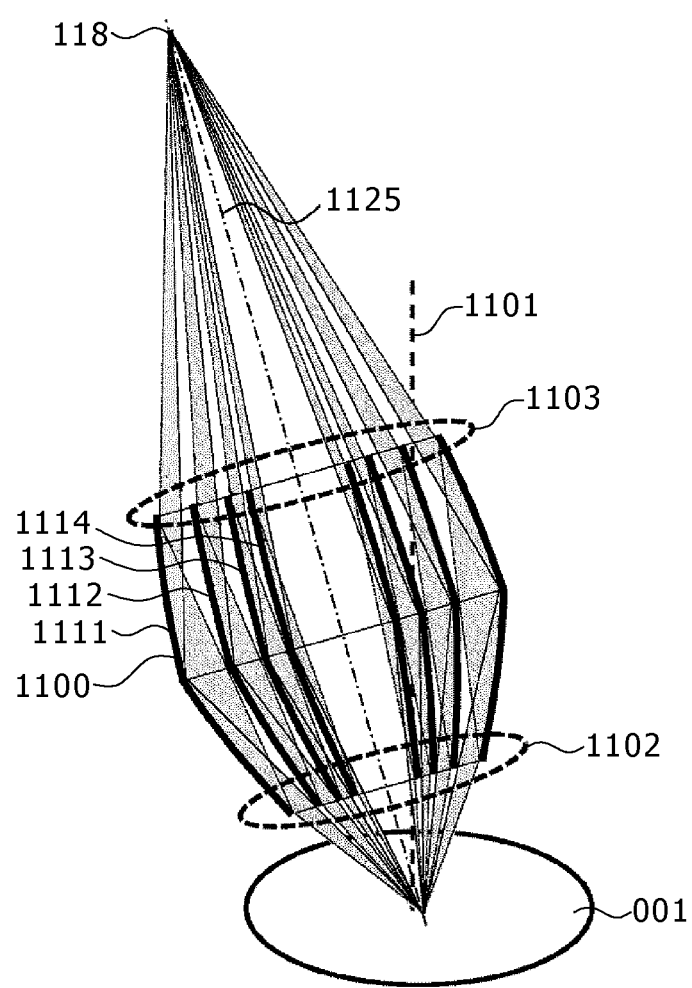
FIG. 12 is an explanatory diagram of a third embodiment (part 1).
Figure 13:
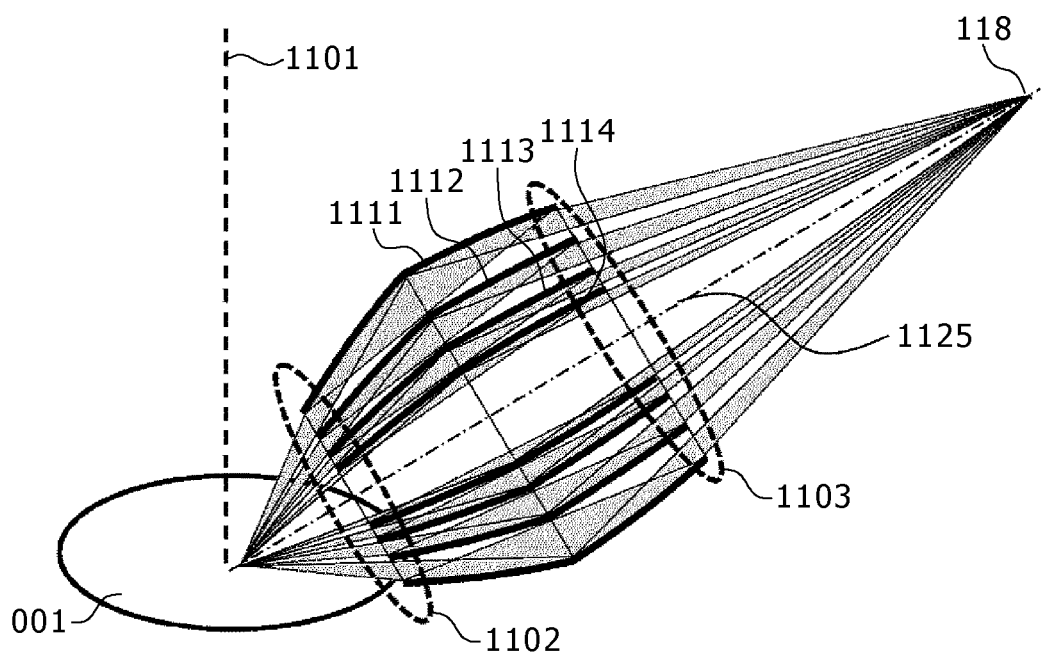
FIG. 13 is an explanatory diagram of the third embodiment (part 2).

FIGS. 12 and 13 are diagrams for explaining this embodiment. In FIG. 12, the Wolter optical system 1100 is arranged in such a manner that the normal 1101 on which the wafer 1101 is to be placed passes through its light-converging end 1102 and its light-exiting end 1103, and its optical axis 1125 is inclined with respect to the normal 1101. In FIG. 13, the Wolter optical system 1100 is arranged in such a manner that the normal 1101 of the surface on which the wafer 001 is to be placed passes outside the light-converging end 1102 and the light-exiting end 1103, and the optical axis 1125 of the Wolter optical system 1100 is inclined with respect to the normal 1101.

Figure 14A:
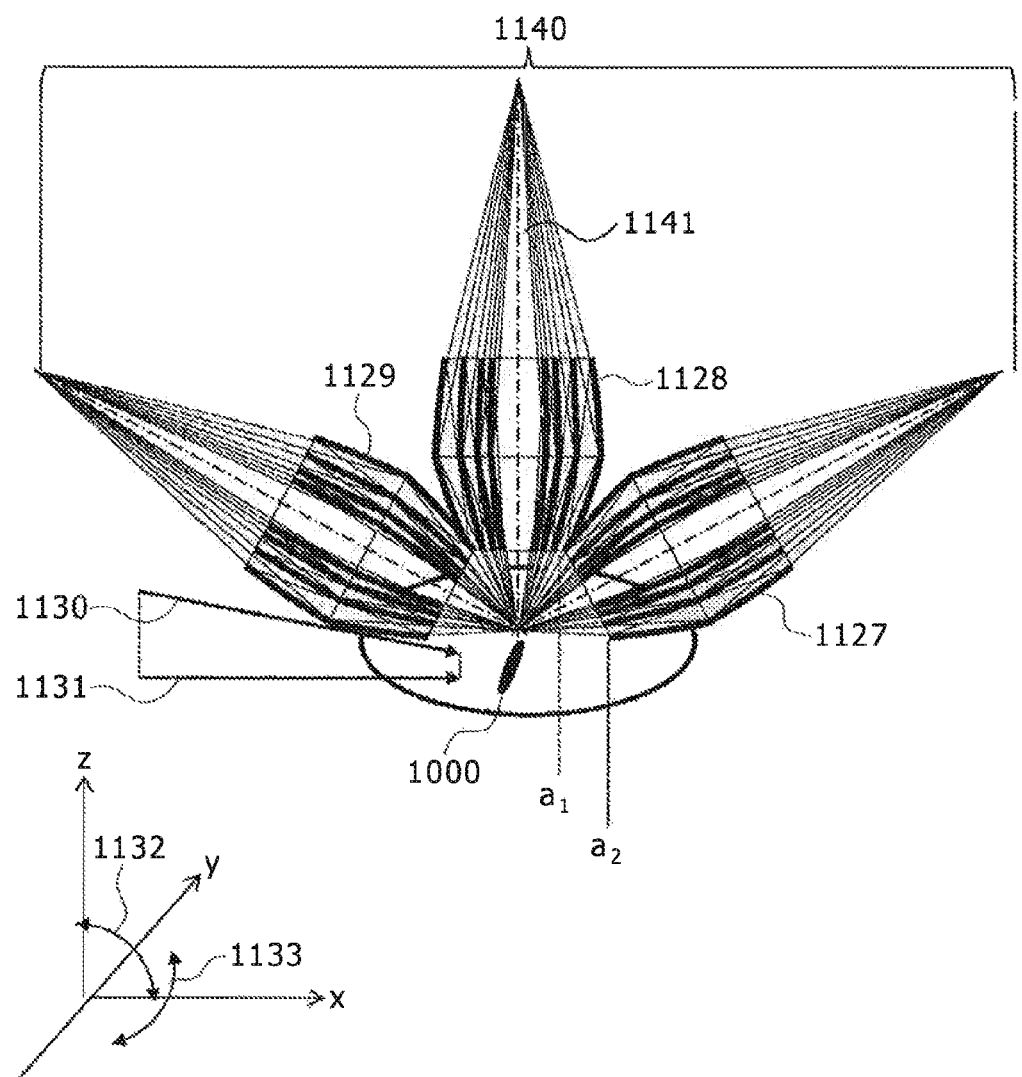
FIGS. 14A and 14B are explanatory diagrams of the third embodiment (part 3).

Further, in this embodiment, a first Wolter optical system 1127, a second Wolter optical system 1128, and a third Wolter optical system 1129 may be used for inspection, as shown in FIG. 14(a). This arrangement enables more scattered light to be converged to form an image. A system including at least one or more Wolter optical systems can be described as a Wolter detection system 1140.

In FIG. 14(a), illuminating light 1130 is supplied onto the wafer 001 at a predetermined angle of incidence from the outside of the Wolter detection system 1140. The first Wolter optical system 1127 is arranged to detect forward scattered light from the illuminated region 1000 to form an image. The second Wolter optical system 1128 detects upward scattered light scattered intensely from the illuminated region 1000 in a wafer normal direction 1141 to form an image. The third Wolter optical system 1129 detects backward scattered light from the illuminated region 1000 to form an image.

The forward scattered light, the backward scattered light, and the upward scattered light can be described in various ways. For example, defining a projection arrow 1131 that is a projection of the illuminating light 1130 onto the wafer 001, light scattered to contain a scattered light component having the same orientation as that of the projection arrow 1131 more than scattered components having other orientations can be described as forward scattered light. Similarly, light scatted to contain a scattered light component having an opposite orientation to an orientation of the projection arrow 1131 more than scattered light components having other orientations can be described as backward scattered light. Further, light scattered to contain a scattered light component in the normal direction of the wafer 001 more than scattered light components having other orientations can be defined as upward scattered light.

Furthermore, in a case of using the first Wolter optical system 1127, the second Wolter optical system 1128, and the third Wolter optical system 1129, it is desirable that the light-converging sides of the first, second, and third Wolter optical systems 1127, 1128, and 1129 are closer to the wafer 001. This is because such an arrangement allows more scattered light to be taken in. Especially, the position of the second Wolter optical system 1128 is restricted by the lengths in an elevation-angle direction 1132 of the first and third Wolter optical systems 1127 and 1129 on the light-conversing sides thereof.

Figure 14B:
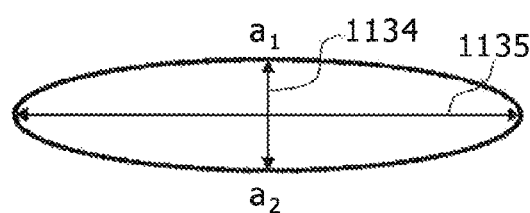

Therefore, the shape at the light-converging end of at least one of the first and third Wolter optical system 1127 and 1129 is designed in such a manner that the length in the elevation-angle direction 1132 is shorter and the length in an azimuth direction 1133 is longer than the length in the elevation-angle direction 1132, as shown in FIG. 14 (b). This design allows the second Wolter optical system 1128 to be close to the wafer 001. In other words, it is also possible to describe that the shape of the light-converging end of at least one of the first and third Wolter optical systems 1127 and 1129 is a substantially elliptical shape having a first axis 1134 of a predetermined length and a second axis 1135 longer than the first axis 1134. The substantially elliptical light-converging end can also be employed in the second Wolter optical system 1128. The elevation angle and the azimuth can be described in various ways. When x-axis parallel to the wafer 001 and y-axis and a z-axis that cross the x-axis are defined, an angle between the x-axis and the z-axis can be described as the elevation angle and an angle between the x-axis and the y-axis can be described as the azimuth.

A worker can determine which one of the forward scattered light, the upward scattered light, and the backward scattered light is detected in an arbitrary manner. That is, according to this embodiment, at least one of the forward scattered light, the upward scattered light, and the backward scattered light can be detected.

Fourth Embodiment

Next, a fourth embodiment is described. In the following, a difference between the fourth embodiment and other embodiments is described. One of features of this embodiment is to supply the illuminating light to the wafer 001 via the inside of the Wolter mirror 1100. In other words, it can be described that the Wolter mirror 1100 has a function as an optical waveguide for the illuminating light in addition to a function of detecting the scattered light from the wafer 001 and forming an image.

Figure 15A:
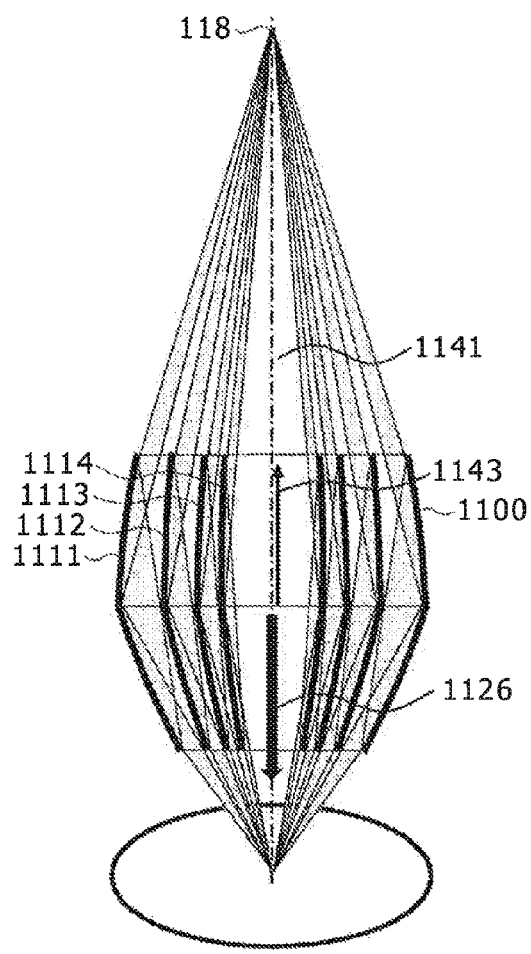
FIGS. 15A and 15B are explanatory diagrams of a fourth embodiment.
Figure 15B:
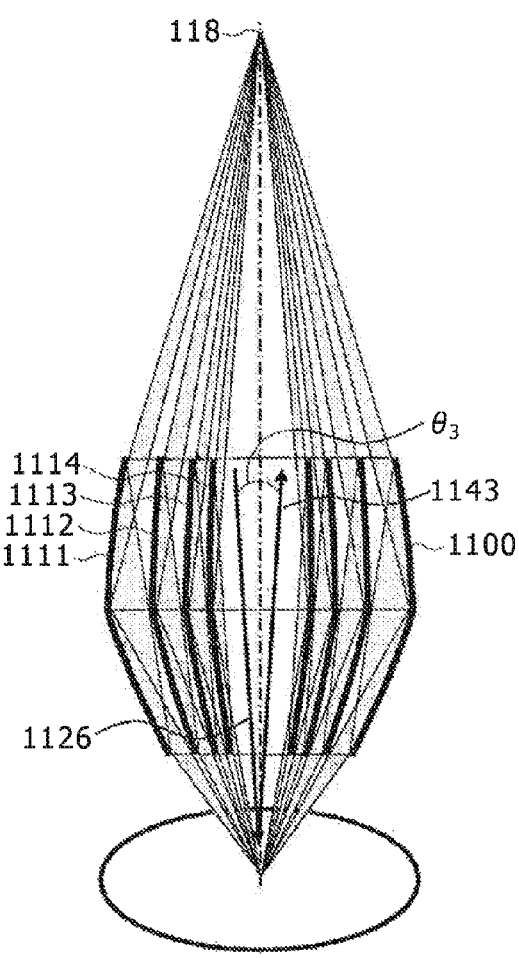

In this embodiment, illuminating light 1126 is supplied to the wafer 001 through the inside of the innermost Wolter mirror 1114 in the Wolter optical system 1100, as shown in FIGS. 15(a) and 15(b). In FIG. 15(a), the illuminating light 1126 is vertical illumination that is coincident with the wafer normal 1141. In FIG. 15(b), the illuminating light 1126 is supplied to the wafer 001 at a relatively small angle of incidence $\theta_3$. Totally reflected light 1143 is generated in cases of FIGS. 15(a) and 15(b). The totally reflected light 1143 may be blocked by blocking means before reaching a point 118 in the path, or may be detected by a detector other from the parallel photon counting sensor for detecting the scattered light. A worker can select whether to block or detect the totally reflected light 1143 in accordance with the type of the defect to be detected.

Fifth Embodiment

Next, a fifth embodiment is described. In the following, a difference between the fifth embodiment and other embodiments is described.

Figure 16A:
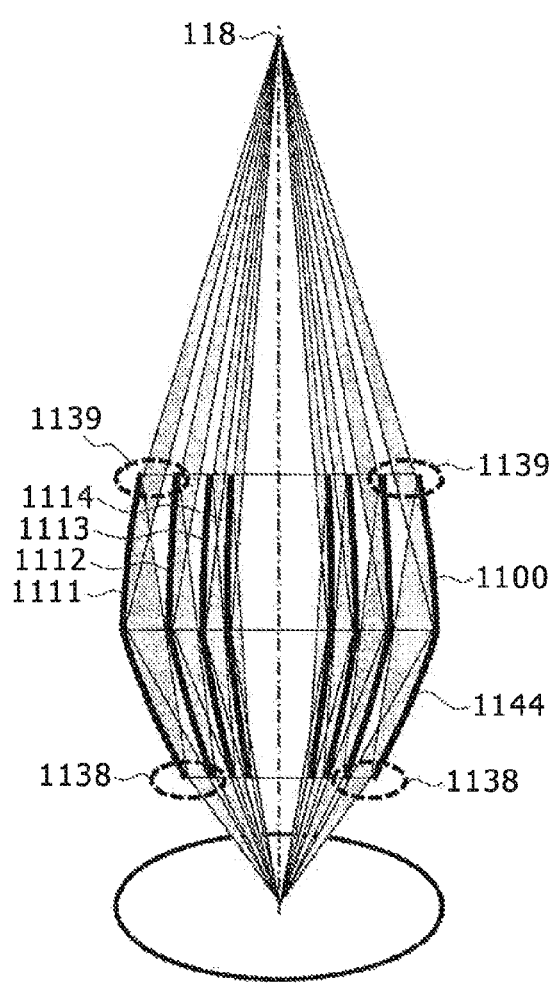
FIGS. 16A-16C are explanatory diagrams of a fifth embodiment.
Figure 16B:
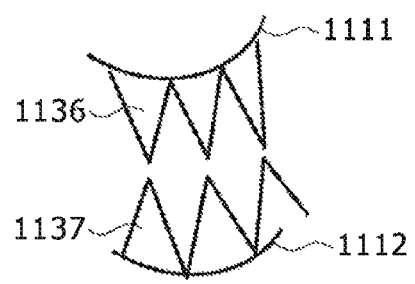
Figure 16C:
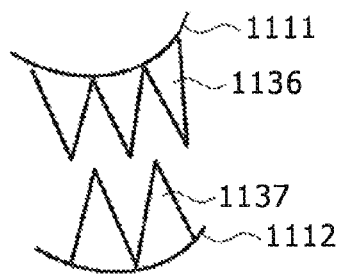

In this embodiment, periodic structures 1136 and 1137 shown in FIG. 16(b) or FIG. 16(c) are formed in at least one of light-converging ends 1138 and light-exiting ends 1139 of the Wolter mirror 1111 and the Wolter mirror 1112, as shown in FIG. 16(a). The periodic structures 1136 and 1137 are formed in a space between the Wolter mirror 1111 and the Wolter mirror 1112. The periodic structures 1136 and 1137 may be serrated. The periodic structures 1136 and 1137 are formed to be symmetric as shown in FIG. 16(b) in some cases, and asymmetric as shown in FIG. 16(c). Those periodic structures 1136 and 1137 may be adapted to the Wolter mirrors 1113 and 1114.

The periodic structures 1136 and 1137 can effectively suppress generation of diffracted light caused by an end portion 1144 of the Wolter optical system 1100, so that a spatial distribution of the scattered light is shaped to a more desirable image.

LIST OF REFERENCE SIGNS

001: wafer
01: control unit
10: illumination optical system unit
101: light source
102: polarized state control means
103: beam shaping unit
104: thin linear converging optical system
1000: illuminated region
1100: Wolter optical system
11a, 11b: detection optical system unit
1111, 1112, 1113, 1114: Wolter mirror
112a, 112b: spatial filter
113a, 113b: polarizing filter
114a, 114b: wavelength filter
115a, 115b: parallel photon counting sensor
12: data processing unit
13: stage unit

The invention claimed is:

1. An inspection device comprising:
   an illuminating optical system configured to supply illuminating light to a sample to form an illuminated region on the sample;
   a detection optical system including a first reflecting optical part configured to converge light from the sample caused by formation of the illuminated region to form an image and a second reflecting optical part arranged to be stacked on the first optical reflecting part;
   a first detector configured to detect light from the first reflecting optical part; and
   a second detector configured to detect light from the second reflecting optical part,
   wherein an image-forming position of the first reflecting optical part and an image-forming position of the second reflecting optical part are different from each other.

2. The inspection device according to claim 1, wherein the first reflecting optical part and the second reflecting optical part are Wolter mirrors.

3. The inspection device according to claim 2, wherein the illuminating light includes x-rays, vacuum ultraviolet rays, or a plurality of wavelengths.

4. The inspection device according to claim 3, comprising a photon counting detection system configured to detect light from the detection optical system.

5. The inspection device according to claim 4, comprising a spatial filter system in an optical path between the detection optical system and the photon counting detection system.

6. The inspection device according to claim 5, comprising a polarizing filter system in an optical path between the detection optical system and the photon counting sensor.

7. The inspection device according to claim 6,
wherein the photon counting detection system includes a first photon counting detection sensor and a second photon counting detection sensor,
a splitting element is arranged on light-exiting sides of the first reflecting optical part and the second reflecting optical part,
light transmitted through the splitting element is detected by the first photon counting detection sensor, and
light reflected by the splitting element is detected by the second photon counting detection sensor.

8. The inspection device according to claim 7,
wherein the spatial filter system includes a first spatial filter and a second spatial filter,
the first spatial filter is arranged between the splitting element and the first photon counting detection sensor, and
the second spatial filter is arranged between the splitting element and the second photon counting detection sensor.

9. The inspection device according to claim 8,
wherein the spatial filter system includes a first polarizing filter and a second polarizing filter,
the first polarizing filter is arranged between the splitting element and the first photon counting detection sensor, and
the second polarizing filter is arranged between the splitting element and the second photon counting detection sensor.

10. The inspection device according to claim 9,
wherein the first detector or the second detector detects at least one of forward scattered light, upward scattered light, and backward scattered light.

11. The inspection device according to claim 10,
wherein the first detector or the second detector detects at least two of the forward scattered light, the upward scattered light, and the backward scattered light.

12. The inspection device according to claim 1, comprising a detection system configured to detect light from the detection optical system.

13. The inspection device according to claim 12, comprising a spatial filter system between the first and second detectors and the detection system.

14. The inspection device according to claim 12, comprising a polarizing filter system between the first and second detectors and the detection system.

15. The inspection device according to claim 2,
wherein the detection optical system includes at least one of an optical system including a first Wolter mirror configured to detect forward scattered light, an optical system including a second Wolter mirror configured to detect upward scattered light, and an optical system including a third Wolter mirror configured to detect backward scattered light.

16. The inspection device according to claim 15,
wherein the detection optical system includes the optical system including the first Wolter mirror, the optical system including the second Wolter mirror, and the optical system including the third Wolter mirror.

17. The inspection device according to claim 16,
wherein a shape of a light-converging end of at least one of the optical system including the first Wolter mirror and the optical system including the third Wolter mirror is a substantially elliptical shape.

18. The inspection device according to claim 17,
wherein the substantially elliptical shape has a first axis in an elevation-angle direction and a second axis longer than the first axis in an azimuth direction.

19. The inspection device according to claim 1,
wherein the detection optical system includes a periodic structure at at least one of a light-converging end and a light-exiting end.

20. The inspection device according to claim 19,
wherein the detection optical system includes a plurality of stacked Wolter mirrors, and
the periodic structure is formed in a space between the plurality of Wolter mirrors.

* * * * *